United States Patent [19]

Gaertner

[11] 4,312,662

[45] Jan. 26, 1982

[54] N-SUBSTITUTED CARBOXY-N-PHOSPHONOMETHYLGLY-CINES AND THE SALTS THEREOF AS HERBICIDES

[75] Inventor: Van R. Gaertner, Ballwin, Mo.

[73] Assignee: Monsanto Company, St. Louis, Mo.

[21] Appl. No.: 108,727

[22] Filed: Dec. 31, 1979

[51] Int. Cl.³ .................... A01N 57/26; C07C 125/06
[52] U.S. Cl. ........................................ 71/86; 560/132; 560/157; 560/167
[58] Field of Search .................... 71/86; 560/157, 167, 560/132

[56] References Cited

U.S. PATENT DOCUMENTS 3,455,675  7/1969  Irani .................................... 71/86
3,799,758  3/1974  Franz .................................. 71/86

*Primary Examiner*—Anton H. Sutto
*Attorney, Agent, or Firm*—Gordon F. Sieckmann; Donald W. Peterson

[57] ABSTRACT

This disclosure relates to novel N-substituted carboxy-N-phosphonomethylglycines and the salts thereof which are useful as herbicides. This disclosure further relates to herbicidal compositions containing such N-substituted carboxy-N-phosphonomethylglycines and the salts thereof and to herbicidal methods employing such compounds and compositions.

9 Claims, No Drawings

N-SUBSTITUTED CARBOXY-N-PHOSPHONOMETHYLGLYCINES AND THE SALTS THEREOF AS HERBICIDES

This invention relates to novel N-substituted carboxy-N-phosphonomethylglycines and the salts thereof which are useful as herbicides. This invention further relates to herbicidal compositions containing such N-substituted carboxy-N-phosphonomethylglycines and the salts thereof and to herbicidal methods employing such compounds and compositions.

U.S. Application Ser. No. 957,765 discloses N-benzyloxycarbonyl-N-phosphonomethylglycine derivatives of the formula

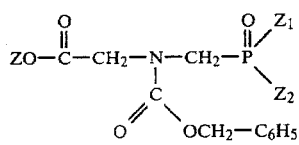

wherein Z is selected from the group consisting of lower alkyl, chlorinated lower alkyl, lower alkoxyalkyl and lower alkoxyalkoxyalkyl and $Z_1$ and $Z_2$ are each selected from the group consisting of halogen, hydroxy, alkalimetaloxy, ammoniumoxy and alkylammoniumoxy; which are useful as herbicides.

U.S. Application Ser. No. 957,766 discloses N-benzyloxycarbonyl derivatives of N-phosphonomethylglycine of the formula

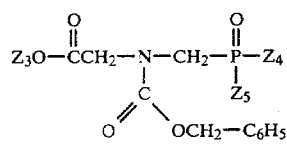

wherein $Z_3$ is selected from the group consisting of lower alkyl, lower chloroalkyl, lower alkoxyalkyl and lower alkoxyalkoxyalkyl and $Z_4$ and $Z_5$ are each selected from the group consisting of lower alkoxy, cyanoalkoxy, alkenylthio, alkylthio, phenylalkylthio, phenylthio and substituted thio; which are useful as herbicides.

U.S. Application Ser. No. 973,318 now U.S. Pat. No. 4,211,732, issued July 8, 1980 to John E. Franz et al discloses N-carbobenzoxy-N-phosphinothioylmethylglycine derivatives of the formula

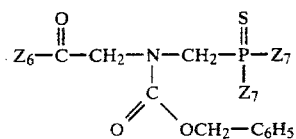

wherein $Z_6$ is selected from the class consisting of alkyl, chloroalkyl, alkoxyalkyl, and each $Z_7$ is selected from the class consisting of alkoxy, thioalkyl, phenoxy, substituted phenoxy, phenylthio and substituted phenylthio; which are useful as herbicides.

The compounds of the present invention are represented by the formula

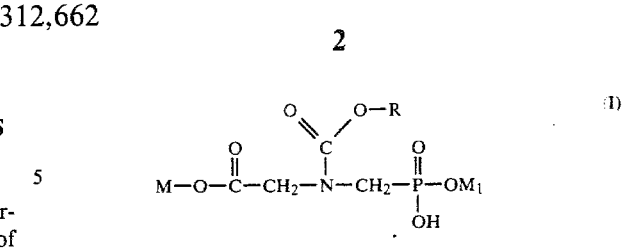

wherein R is selected from the group consisting of $C_1$-$C_8$ alkyl, $C_2$-$C_4$ alkenyl, $C_2$-$C_4$ alkynyl, $C_1$-$C_8$ haloalkyl, $C_2$-$C_4$ haloalkenyl, $C_2$-$C_4$ haloalkynyl and phenyl; and M and $M_1$ are independently hydrogen or alkali metal.

As used herein, the term "alkali metal" refers to lithium, sodium, potassium and the like. It is preferred that the alkali metals represented by M or $M_1$ are sodium or potassium.

As employed herein, the term "$C_1$-$C_8$ alkyl" designates those alkyl radicals which have up to 8 carbon atoms in a straight or branched chain, such as, for example, methyl, ethyl, propyl, isopropyl, butyl, t-butyl, pentyl, n-hexyl, n-octyl and the like.

Groups illustrative of the "$C_2$-$C_4$ alkenyl" and "$C_2$-$C_4$ alkynyl" radicals represented by R include alkenyl and alkynyl radicals having from 2 to 4 carbon atoms such as vinyl, allyl, propenyl, butenyl, acetylenyl, propynyl, butynyl and the like.

The terms "haloalkyl", "haloalkenyl" and "haloalkynyl" refer to alkyl groups having from one to eight carbon atoms and alkenyl and alkynyl having from one to four carbon atoms wherein at least one hydrogen atom has been replaced by a halogen atom. Groups representative of these radicals include trichloromethyl, dibromobutyl, fluorooctyl, chlorobutenyl, iodobutynyl and the like. It is preferred that M and $M_1$ are either both alkali metal or both hydrogen. It is more preferred that M and $M_1$ are both hydrogen.

In accordance with the present invention, the compounds of formula (I) wherein M and $M_1$ are alkali metal are prepared by reacting an aqueous solution containing a compound of the formula

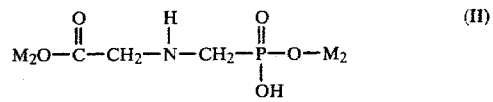

wherein $M_2$ is an alkali metal; with a chloroformate of the formula

wherein R is above defined; within a temperature range of 0°–20° C. to produce a compound of the formula

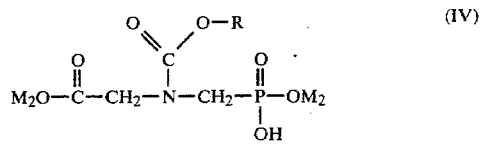

For ease of reaction and recovery of product, it is preferred to conduct the process of the present invention within a range of 10°–15° C.

In preparing the compounds of formula (IV), the ratio of reactants can vary over a wide range. It is preferred to employ an excess of a chloroformate of formula (III) for ease of reaction and maximum yield of product.

While the process of this invention can be conducted at atmospheric, sub-atmospheric or super-atmospheric pressure, for convenience and economy it is generally preferred to conduct these processes at atmospheric pressure.

The compound of formula (IV) can be used without isolation or purification, or it can be acidified to remove the alkali metal. Although acidification may be accomplished in some cases by treatment with hydrochloric acid, it is preferred to acidify the compounds of formula (IV) via ion exchange chromatography using an ion exchange resin in the acid form.

The following illustrative, non-limiting examples will serve to further demonstrate to those skilled in the art the manner in which the specific compounds within the scope of this invention can be prepared. In the examples, all parts are parts by weight unless otherwise expressly stated.

EXAMPLE 1

To a stirred solution containing 10.7 g (0.05 mol) of disodium-N-phosphonomethylglycine in water at a temperature of 10°-15° C. was slowly added 6.6 g (0.055 mol) of allylchloroformate. While maintaining the temperature below 20° C., a 50% sodium hydroxide solution was slowly added to the reaction mixture until the pH of the resulting mixture stabilized at a phenolphthalein endpoint. While maintaining the temperature of the reaction mixture below 10° C., the reaction mixture was acidified using concentrated hydrochloric acid, filtered and the filtrate was then treated with ethanol. The treated filtrate was filtered to remove residual sodium chloride, then concentrated and the concentrate was passed over an acid Dowex-50 ion exchange resin. Methanol was added to the eluate forming a suspension. The suspension was filtered and the filtrate was chromatographed over acid Dowex-50 ion exchange resin. The eluate was concentrated and the residue was dried over potassium hydroxide in vacuo yielding a crude product. The crude product was broken up and redried at 100° C. and 1 mm Hg to yield N-allyloxycarbonyl-N-phosphonomethylglycine trihydrate (8.7 g; 57% yield) having the following analysis: Calculated: C, 27.37; H, 5.91; P, 10.08. Found: C, 27.05; H, 4.71; P, 9.76.

EXAMPLE 2

To a stirred solution containing 21.3 (0.1 mol) of disodium-N-phosphonomethylglycine in water at a temperature of 10°-15° C. was slowly added 17.5 g (0.105 mol) of 4-chloro-2-butynyl chloroformate. A 50% sodium hydroxide solution was slowly added to the reaction mixture to a phenolphthalein endpoint. The addition of the sodium hydroxide solution was repeated until the phenolphthalein endpoint was stable. The resulting mixture was extracted with diethyl ether. The layers were separated and the aqueous layer was acidified with hydrochloric acid, then passed over acid Dowex-50 ion exchange resin. The eluate was concentrated in vacuo yielding a residual gum which was dried over potassium hydroxide pellets (at 1 mm Hg) to yield N-[(4-chloro-2-butynyl)oxy]carbonyl-N-phosphonomethylglycine (11.3 g; 38% yield) as a tan glass having the following analysis: Calculated: Cl, 11.83; P, 10.34. Found: Cl, 12.82; P, 11.03.

EXAMPLE 3

To a stirred mixture containing 16.9 g (0.10 mol) of N-phosphonomethyglycine and 16 g (0.20 mol) of a 50% solution of sodium hydroxide in 30 ml. of water at 15° C. was added 15.6 g (0.10 mol) of phenyl chloroformate. After stirring the mixture for one hour, a 50% sodium hydroxide solution was added to the mixture until a phenolphthalein endpoint was reached. The addition of the sodium hydroxide solution was repeated until the phenolphthalein endpoint was stable at 20°-25° C. To the reaction mixture was added an additional 1.6 g (0.01 mol) of phenyl chloroformate and the resulting mixture was made alkaline (phenolphthalein endpoint) using a 50% sodium hydroxide solution. A suspended solid formed in the reaction mixture. To the reaction mixture was added 100 ml. of water and the mixture was then filtered to remove any traces of a solid residue. The filtrate was concentrated and the residue was dried over potassium hydroxide pellets in vacuo. A portion of the residue (15 g) was redissolved in water and the aqueous solution was slowly acidified with hydrochloric acid until a precipitate formed. The acidified solution was filtered and the precipitate was washed with water and dried to yield N-phenoxycarbonyl-N-phosphonomethylglycine, sodium salt (6.4 g; 73% yield) as a white powder which decomposed at 260°-280° C. having the following analysis: Calculated: C, 38.60; H, 3.56; P, 9.95. Found: C, 38.96; H, 4.09; P, 9.81.

EXAMPLE 4

To a stirred mixture containing 16.9 g (0.10 mol) of N-phosphonomethylglycine and 16 g (0.20 mol) of a 50% solution of sodium hydroxide in 30 ml. of water at 10°-12° C. was added 11.2 g (0.12 mol) of methyl chloroformate. After stirring the mixture for 2 hours, a 50% sodium hydroxide solution was slowly added to the mixture until a mixture having a pH of 8 was obtained. To the reaction mixture was added an additional 3.0 g (0.03 mol) of methyl chloroformate and the resulting mixture was made alkaline (to a phenolphthalein endpoint) using a 50% sodium hydroxide solution. The reaction mixture was concentrated and dried over potassium hydroxide pellets to yield N-methoxycarboxyl-N-phosphonomethylglycine, disodium salt which decomposed at 140° C.

EXAMPLE 5

To a stirred mixture containing 16.9 g (0.10 mol) of N-phosphonomethylglycine and 16 g (0.20 mol) of a 50% solution of sodium hydroxide in 30 ml. of water at 10°-15° C. was added 10.8 g (0.10 mol) of ethyl chloroformate. After stirring the reaction mixture for 3 hours, an additional 16 g (0.20 mol) of a 50% sodium hydroxide solution was added to the mixture. An additional 3.5 g (0.03 mol) of ethyl chloroformate was then added to the reaction mixture at 25° C. The resulting mixture was stirred for 30 minutes after which time a 50% sodium hydroxide solution was added to the reaction mixture until a phenolphthalein endpoint was reached. The reaction mixture was concentrated in vacuo and the residue was dried over potassium hydroxide to yield a crude product. The crude product was broken up and redried over potassium hydroxide pellets to yield N-ethoxycarbonyl-N-phosphonomethylglycine, disodium salt, which decomposed at 200°-230° C.

EXAMPLE 6

To a stirred solution containing 16.9 g (0.10 mol) of disodium-N-phosphonomethylglycine in water at 20°-25° C. was added 15 g (0.11 mol) of n-butyl chloroformate. After stirring the reaction mixture for 2 hours, a 50% sodium hydroxide solution was slowly added until the pH of the mixture stabilized at a phenolphthalein endpoint. The reaction mixture was concentrated and the residue dried over potassium hydroxide pellets to yield 42.3 g of N-n-butoxycarbonyl-N-phosphonomethylglycine, disodium salt, as a white solid having the following analysis: Calculated: C, 33.00; H, 5.19; P, 10.64. Found: C, 32.77; H, 5.16; P, 10.69.

EXAMPLE 7

To a stirred mixture containing 16.9 g (0.10 mol) of N-phosphonomethylglycine and 24 g (0.30 mol) of a 50% solution of sodium hydroxide in 30 ml. of water at 10°-15° C. was added 18.0 g (0.11 mol) of n-hexyl chloroformate. The resulting mixture was allowed to stand for 16 hours after which time an additional 4.1 g (0.025 mol) of n-hexyl chloroformate was added at 20° C. While maintaining the temperature at 20° C., a 50% sodium hydroxide solution was then added to the reaction mixture until a phenolphthalein endpoint was stable. The resulting mixture was extracted with diethyl ether and benzene. The aqueous layer was separated, concentrated in vacuo and dried over potassium hydroxide pellets in vacuo to yield 41.1 g of a crude product. A portion of the crude product (15 g) was dissolved in water and then recrystallized using methanol and dried at 50° C., (below 1 mm Hg) to yield N-n-hexoxycarbonyl-N-phosphonomethylglycine, disodium salt dihydrate, as translucent crystals which decomposed upon heating and having the following analysis: Calculated: C, 31.84; H, 5.88; P, 8.21. Found: C, 31.78; H, 4.71; P, 8.48.

EXAMPLE 8

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two or three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

A—Canada Thistle*
B—Cocklebur
C—Velvetleaf
D—Morningglory
E—Lambsquarters
F—Smartweed
G—Yellow Nutsedge*
H—Quackgrass*
I—Johnsongrass*
J—Downy Brome
K—Barnyardgrass
L—Soybean
M—Sugar Beet
N—Wheat
O—Rice
P—Sorghum
Q—Wild Buckwheat
R—Hemp Sesbania
S—Panicum Spp
T—Crabgrass

*Established from vegetative propagules.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 4 | 11.2 | 3 | 3 | 2 | 2 | 4 | 4 | 2 | 4 | 4 | 4 | 3 |
| 1 | 4 | 5.6 | 3 | 3 | 1 | 4 | 4 | 4 | 2 | 3 | 3 | 2 | 3 |
| 2 | 4 | 11.2 | 1 | 1 | 0 | 2 | 1 | 1 | 2 | 1 | 1 | 0 | 2 |
| 3 | 2 | 11.2 | 0 | 0 | 0 | 0 | 0 | 0 | 0 | 0 | 0 | 0 | 0 |
| 3 | 4 | 56.0 | 1 | 2 | 0 | 1 | 2 | 0 | 1 | 1 | 0 | 0 | 1 |
| 4 | 2 | 11.2 | 0 | 0 | 0 | 0 | — | 0 | 0 | 0 | 0 | 0 | 0 |
| 5 | 2 | 11.2 | — | 0 | 0 | 1 | 2 | 0 | 0 | 1 | 0 | 0 | 0 |
| 6 | 2 | 11.2 | 0 | 0 | 0 | 0 | 0 | 0 | 0 | 0 | 0 | 0 | 0 |

TABLE I-continued

| Compound of Example No. | WAT | kg/h | A | B | C | D | E | F | G | H | I | J | K |
|---|---|---|---|---|---|---|---|---|---|---|---|---|---|
| 7 | 2 | 11.2 | — | 0 | 0 | 0 | 0 | 0 | 0 | 1 | 0 | 0 | 0 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 1 | 3 | 3 | 3 | 2 | 2 | 1 | 2 | 0 | 1 | 4 | 2 | 1 | 3 | 3 | 4 |
| 1 | 4 | 1.12 | 0 | 2 | 2 | 0 | 2 | 2 | 0 | 1 | 0 | 1 | 1 | 2 | 4 | 1 | 3 |  |
| 1 | 2 | 0.28 | 0 | 1 | 1 | 0 | 0 | 0 | 0 | 0 | 0 | 0 | 0 | 0 | 0 | 0 | 1 |  |

EXAMPLE 9

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table III.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the table are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| 1 | 2 | 11.2 | 0 | 0 | 0 | 0 | 0 | 0 | 0 | 0 | 0 | 0 | 0 |
| 2 | 2 | 11.2 | 0 | 0 | 0 | 0 | 0 | 0 | 0 | 0 | 0 | 0 | 0 |
| 3 | 2 | 11.2 | 0 | 0 | 0 | 0 | 0 | 0 | 0 | 0 | 0 | 0 | 0 |
| 3 | 2 | 56.0 | 2 | 0 | 0 | 0 | 0 | 0 | 0 | 0 | 3 | 0 | 0 |
| 4 | 2 | 11.2 | 0 | — | 0 | 0 | 3 | 0 | 0 | 0 | 0 | 0 | 0 |
| 5 | 2 | 11.2 | 0 | 0 | 0 | 0 | 0 | 0 | 0 | 0 | 0 | 0 | 0 |
| 6 | 2 | 11.2 | 0 | 0 | 1 | 0 | 0 | 0 | 0 | 0 | 0 | 0 | — |
| 7 | 2 | 11.2 | 0 | 0 | 0 | 0 | 0 | 0 | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfalrl as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of controlling undesired plants which comprises contacting said plants or the plant growth medium with a herbicidal amount of a compound of the formula

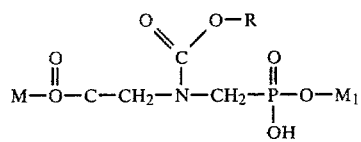

wherein R is selected from the group consisting of $C_1$–$C_8$ alkyl, $C_2$–$C_4$ alkenyl, $C_2$–$C_4$ alkynyl, $C_2$–$C_4$ haloalkynyl and phenyl; and M and $M_1$ are independently hydrogen or alkali metal.

2. A method according to claim 1 wherein R is $C_2$–$C_4$ alkenyl or $C_2$–$C_4$ alkynyl.

3. A method according to claim 2 wherein the compound is N-allyloxycarbonyl-N-phosphonomethylglycine.

4. A compound of the formula

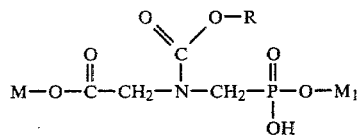

wherein R is selected from the group consisting of $C_1$–$C_8$ alkyl, $C_2$–$C_4$ alkenyl, $C_2$–$C_4$ alkynyl, $C_2$–$C_4$ haloalkynyl and phenyl; and M and $M_1$ are independently hydrogen or alkali metal.

5. A compound according to claim 4 wherein R is $C_2$–$C_4$ alkenyl or $C_2$–$C_4$ alkynyl.

6. A compound according to claim 5 wherein the compound is N-allyloxycarbonyl-N-phosphonomethylglycine.

7. A herbicidal composition comprising an inert adjuvant and a herbicidally effective amount of a compound of the formula

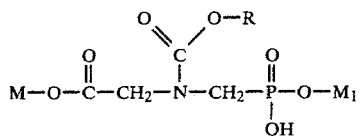

wherein R is selected from the group consisting of $C_1$–$C_8$ alkyl, $C_2$–$C_4$ alkenyl, $C_2$–$C_4$ alkynyl, $C_2$–$C_4$ haloalkynyl and phenyl; and M and $M_1$ are independently hydrogen or alkali metal.

8. A composition according to claim 7 wherein R is $C_2$–$C_4$ alkynyl.

9. A composition according to claim 8 wherein the compound is N-allyloxycarbonyl-N-phosphonomethylglycine.

* * * * *